United States Patent
Petersen et al.

(10) Patent No.: US 6,891,984 B2
(45) Date of Patent: May 10, 2005

(54) SCANNING MINIATURE OPTICAL PROBES WITH OPTICAL DISTORTION CORRECTION AND ROTATIONAL CONTROL

(75) Inventors: Christopher L. Petersen, Carlisle, MA (US); Edward I. McNamara, Chemsford, MA (US); Ronald B. Lamport, Pelham, NH (US); Michael Atlas, Arlington, MA (US); Joseph M. Schmitt, Andover, MA (US); Paul Magnin, Andover, MA (US); Eric A. Swanson, Acton, MA (US)

(73) Assignee: LightLab Imaging, LLC, Westford, MA (US)

( * ) Notice: Subject to any disclaimer, the term of this patent is extended or adjusted under 35 U.S.C. 154(b) by 169 days.

(21) Appl. No.: 10/205,374

(22) Filed: Jul. 25, 2002

(65) Prior Publication Data

US 2004/0017961 A1 Jan. 29, 2004

(51) Int. Cl.[7] .................................................. G02B 6/00
(52) U.S. Cl. ..................... 385/12; 385/117; 600/137; 600/342; 600/478
(58) Field of Search ........................ 385/12, 123, 117, 385/118, 13, 116, 25; 600/478, 342, 101, 137, 160

(56) References Cited

U.S. PATENT DOCUMENTS

| | | | |
|---|---|---|---|
| 4,456,330 A | | 6/1984 | Bludau |
| 4,740,047 A | | 4/1988 | Abe et al. |
| 5,127,405 A | * | 7/1992 | Alcala et al. ............... 600/342 |
| 5,321,501 A | | 6/1994 | Swanson et al. |
| 5,339,378 A | | 8/1994 | Simonds et al. |
| 5,428,699 A | | 6/1995 | Pon |
| 5,443,781 A | * | 8/1995 | Saab ........................ 264/291 |
| 5,456,245 A | * | 10/1995 | Bornhop et al. ............ 385/117 |
| 5,459,570 A | | 10/1995 | Swanson et al. |
| 5,501,226 A | | 3/1996 | Petersen et al. |

(Continued)

FOREIGN PATENT DOCUMENTS

| | | |
|---|---|---|
| JP | 2000262461 | 2/2000 |
| WO | WO 98/38907 | 9/1998 |
| WO | WO 01/11409 A3 | 2/2001 |
| WO | WO 01/11409 A2 | 2/2001 |

OTHER PUBLICATIONS

Shiraishi et al., "Integration–Oriented Lensed Fibers Having Long Working Distances and Wide Tolerances," Proceedings of the Optical Fiber Communication Conference, OFC (1996), San Jose California, vol. 2, paper #ThK4, pps 245–246, Feb. 25–Mar. 1, 1996.

Hillerich, "Shape Analysis and Coupling Loss of Microlenses on Single–Mode Fiber Tips," Journal of Lightwave Technology, Applied Optics, vol. 27, pps. 3102–3106 (Aug., 1998).

Prince et al., "Ball–Tipped Fibers for Laser Angioplasty with the Pulsed–Dye Laser," IEEE Journal of Quantum Electronics, vol. 26, pps. 2297–2304, Dec. 1990.

Vaidya et al., "Sculpted Optical Silica Fiber Tips for Use in Nd:YAG Contact Tip Laser Surgery: Part 1– Fabrication Techniques," Optical Engineering, vol. 31, pps. 1404–1409, (Jul. 1992).

PCT International Search Report for International Application No.: PCT/US03/23019 Dec.2003.

*Primary Examiner*—Jared J. Fureman
(74) *Attorney, Agent, or Firm*—Kirkpatrick & Lockhart Nicholson Graham LLP

(57) ABSTRACT

Optical probes having a diameter less than substantially 500 $\mu$m for use in scanning light from a long, highly flexible fiber to a sample. In one embodiment the probe includes a viscous damping fluid suitable to prevent non-uniform rotational distortion (NURD).

27 Claims, 14 Drawing Sheets

U.S. PATENT DOCUMENTS

| | | |
|---|---|---|
| 5,699,464 A | 12/1997 | Marcuse et al. |
| 5,800,666 A | 9/1998 | Bonham, Jr. et al. |
| 6,014,483 A | 1/2000 | Thual et al. |
| 6,033,383 A * | 3/2000 | Ginsburg .................... 604/113 |
| 6,069,656 A | 5/2000 | Silver |
| 6,069,698 A * | 5/2000 | Ozawa et al. ............... 356/511 |
| 6,134,003 A | 10/2000 | Tearney et al. |
| 6,144,791 A | 11/2000 | Wach et al. |
| 6,165,127 A | 12/2000 | Crowley |
| 6,208,887 B1 * | 3/2001 | Clarke ........................ 600/478 |
| 6,383,209 B1 * | 5/2002 | Crowley ..................... 600/478 |
| 6,445,939 B1 * | 9/2002 | Swanson et al. ............ 600/342 |
| 6,485,413 B1 * | 11/2002 | Boppart et al. ............. 600/478 |
| 6,547,757 B1 * | 4/2003 | Kranz et al. ................ 600/478 |
| 6,564,087 B1 * | 5/2003 | Pitris et al. ................. 600/478 |
| 6,615,072 B1 | 9/2003 | Izatt et al. |
| 2002/0041724 A1 * | 4/2002 | Ronnekleiv et al. .......... 385/12 |
| 2004/0086215 A1 * | 5/2004 | Salerno et al. ................ 385/12 |

\* cited by examiner

SCANNING MINIATURE OPTICAL PROBES WITH OPTICAL DISTORTION CORRECTION AND ROTATIONAL CONTROL

FIELD OF INVENTION

The field of invention relates to the design, fabrication, and use of ultra-small scanning imaging probes and more particularly to the design and fabrication and use of an ultra-small scanning imaging probes for prevention of rotational distortion.

BACKGROUND OF INVENTION

There is a pressing need for developing ultra-small scanning optical probes. These probes require ultra-small imaging lenses and associated scanning and beam director elements. Such probes are used in Optical Coherence Tomography (OCT) and other interferometric imaging and ranging systems, as well as for delivery of other imaging modalities (e.g. fluorescence) or therapeutic optical sources. Future medical (and nonmedical) optical probes will require these miniature probes to navigate small and torturous passageways such as arteries, veins, and pulmonary airways. Present technology generally is not adequate for meeting the needs of these small probes when the probes must be less than ~500 µm in diameter, while simultaneously having a working distance that can extend up to several millimeters and performing controlled and potentially complex scan patterns.

Although the design and construction of small lenses is known, as exemplified by a design of a catheter that uses a small (~1 mm) GRIN lens coupled to a fold mirror for imaging the aperture of a single-mode fiber onto a vessel wall, the scaling of this design to less than 500 µm is problematic. Although techniques exist for making very small lenses that have small working distances suitable for coupling to laser diodes and other optical components, these lenses generally do not offer the >1 mm working distance and the >1 mm depth-of-field required for many applications.

Further, there are a number of commercially available 'torque wires'—miniature wire-wound devices intended to transmit torque over a long and flexible shaft. Such devices are now commonly used in intravascular ultrasound (IVUS) procedures. Such ultrasound probes combined with torque wires perform rotational scanning in coronary arteries. Generally however, these devices are at least 1 mm in diameter, and are thus 2 to 4 times larger than the devices required by many applications. Presently, such torque wires are not scalable to the sizes required to permit the construction of small optical scanning probes.

U.S. Pat. No. 6,165,127 ('127) discloses the use of a viscous fluid located inside the bore of an ultrasound catheter. The purpose of the fluid is to provide loading of a torque wire such that the wire enters the regime of high torsional stiffness at moderate spin rates. As described in the '127 patent, this fluid is housed within a separate bore formed inside the main catheter, increasing the overall size of the device, the fluid does not contact the imaging tip, nor does the ultrasound energy propagate through this fluid unlike the present invention.

Finally, achieving uniform rotational scanning at the distal tip of a single fiber, while maintaining an overall device size less than 500 um in diameter is a major challenge. Because it is highly undesirable to add a motor to the distal tip, with the attendant wires and size issues, a way must be found to apply torque to the proximal tip and transmit the torque to the distal tip which may be as much as three meters away in a catheter application. If the extremely low inherent rotational stiffness of a glass fiber is considered (approximately 1 millionth of a N-m of applied torque will cause a 1 cm length of standard 125 µm diameter fiber to twist up one degree) the issues of uniformly spinning the distal tip by driving the proximal end can be appreciated. Uniform rotation is critically important in endoscopic techniques in order to obtain accurate circumferential images. The term 'NURD' (non-uniform rotational distortion) has been coined in the industry to describe these deleterious effects.

The present invention relates to a small optical fiber probe that experiences substantially no NURD.

SUMMARY OF INVENTION

The invention relates to an optical probe including a sheath; a flexible, bi-directionally rotatable optical transmission system positioned within the sheath; and a viscous damping fluid located in the sheath. The optical transmission system is capable of transmitting, focussing, and collecting light of a predetermined range of wavelengths. The sheath and the viscous damping fluid are transparent to at least some of the wavelengths of that light. The index of refraction of the viscous fluid is typically chosen to remove the optical effects induced by propagation through said sheath. In one embodiment, the optical transmission system is less than substantially 300 µm in diameter. In some embodiments, the sheath is substantially cylindrical. In some embodiments the optical probe further comprises a lumen for providing catheter flushes. In other embodiments, the catheter flushes are maintained substantially at body temperature to minimize temperature induced-viscosity changes in the viscous damping fluid.

In another aspect, the optical transmission system includes an optical fiber and a focusing element optically coupled to a beam director. The focusing element creates an exit beam waist having a radius of less than 100 µm with a working distance ranging from zero to several millimeters, and a depth-of-field up to several millimeters. In one embodiment, the sheath is less than substantially 500 µm in diameter. In one embodiment, the transmission fiber is rotatably driven at its proximal end.

In one embodiment, the focussing element and the beam director comprises the transmission fiber attached to a first segment of silica fiber, which is attached to a graded index fiber attached to a second segment of coreless fiber. In another embodiment, the second segment of coreless fiber has one or more angled facets to form the beam director. In yet another embodiment, the focussing element and beam director includes a transmission fiber attached to a graded index fiber whose working aperture and index profile are designed to produce a beam waist with a radius of less than 100 µm at a working distance, measured from the end of the lens, of several millimeters.

DESCRIPTION OF THE PREFERRED EMBODIMENT

Figure 1:
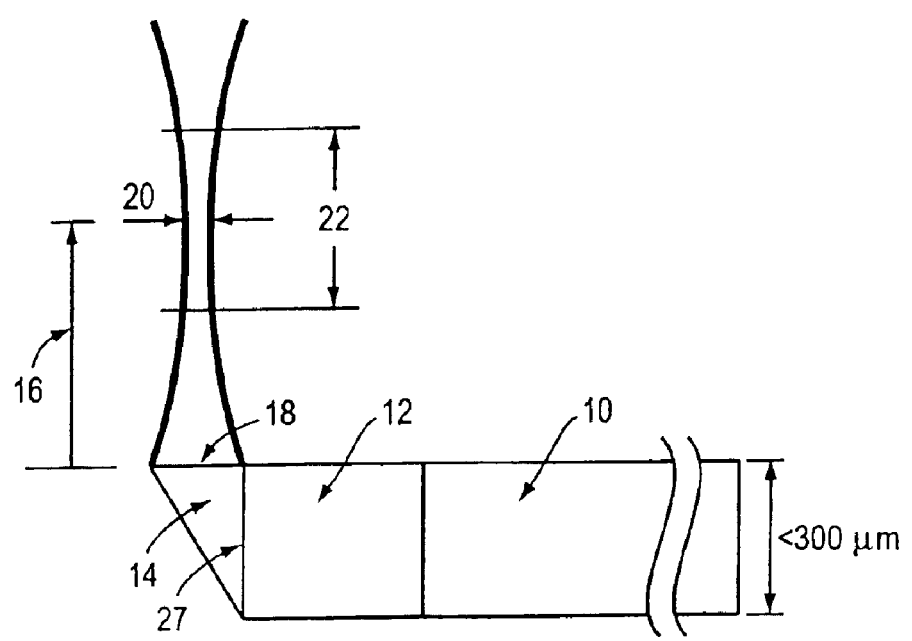
FIG. 1 illustrates an embodiment of an imaging lens according to an illustrative embodiment of the invention.

FIG. 1 shows an example of an embodiment of an imaging lens. In this embodiment a single-mode fiber 10 is spliced or otherwise secured to a lens 12. The lens 12 is approximately the same diameter as the fiber 10. The fiber 10 may include a variety of thin protective coatings. A beam director 14, a 45 (or other suitable angle) degree fold mirror in one embodiment, is affixed to the lens 12 using fusion splicing or glue. The fold mirror 14 is either coated with a high-reflectance material or operates according to the principle of total internal reflection.

Figure 2:
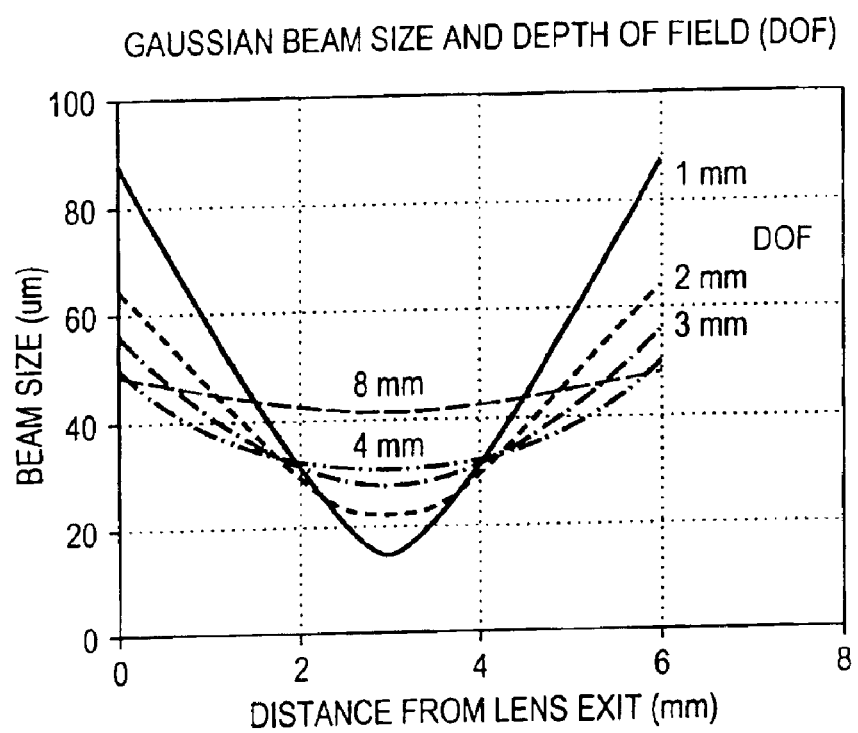
FIG. 2 illustrates the relationship between the spot size and the depth of field for the embodiment of the imaging lens shown in FIG. 1 assuming a Gaussian beam.

Still referring to FIG. 1, in the embodiment shown, the lens 12 has a working distance 16 from the surface 18 of the fold mirror 14 to the waist location 20 of the Gaussian beam. The combination of the lens 12 and beam director 14 magnify (or reduce) the beam waist originally located at the exit of the single-mode fiber 10 and create a new waist 20 at the spot located at the working distance 16. At the working distance 16 the spot size is minimized, as shown in FIG. 2, and the phase front is nearly flat.

In general, in highly multimode beams (mode number of approximately 10 or higher), the waist location 20 and the classical image location are nearly coincident. For the single-mode beams employed here, however, these locations can differ significantly. The lens/imaging system has a depth of focus 22 that is inversely related to the square of the spot size. For many imaging systems, including Optical Coherence Tomographic imaging systems, light emitted from the fiber is focused on a sample and retro-reflected light is then coupled back through the lens and into the single-mode fiber. In these and other imaging or light delivery/collection applications the best optical performance is obtained when the light impinges on a sample that is located within the depth of focus or field 22.

Single-mode Gaussian beams expand from their minimum width (the 'waist' 20) according to the well-known relationship:

$$\omega(z) = \omega_0 \sqrt{1 + \left(\frac{z}{z_0}\right)^2} \quad (1)$$

where $\omega(z)$ is the beam radius at location z, $\omega_0$ is the beam waist which occurs by definition at z=0, and $z_0$ is the Rayleigh range and is the distance at which the peak intensity falls to ½ of its value as measured at the waist. The Rayleigh range is given by $(n\pi\omega_0^2/\lambda)$, where $\lambda$ is the wavelength of the light in a vacuum, and n is the index-of-refraction of the medium. The Rayleigh range thus dictates the depth-of-field 22, which is typically defined as twice $z_0$ and is often called the confocal parameter. As shown in FIG. 1, the distance 16 from the waist location 20 of the imaged beam back to the surface 18 is defined here as the working distance of the lens assembly 12/14. The total focussing length of the lens 12 itself additionally includes the optical path traversed in beam director 14.

The radius of curvature, R(z), of a Gaussian beam follows another well-known relationship:

$$R(z) = z_0 \left(\frac{z}{z_0} + \frac{z_0}{z}\right) \quad (2)$$

Equation 2 demonstrates that a Gaussian beam has an infinite radius of curvature (i.e. flat phase front) at the waist, and that at distances which are large compared to the Rayleigh range, a Gaussian beam will propagate much as a spherical wave centered at z=0 and can be treated in this regime with classical (geometrical) optics. In the case at hand, however, the desired working distance(z) and depth of field($z_0$) are comparable and classical optics cannot be used effectively.

To solve the current problem, a desired working distance 16 and depth of field 22 are first chosen. This determines the required waist size which is to be created by the lens. The required waist size and desired location 16 in space in turn determine the required beam size as well as the phase front radius of curvature (of the outgoing beam) at the lens surface 27. Thus, the lens system 12 must allow the beam to expand from the exit of the fiber to match the beam size required at the lens surface 27, and must also bend the phase front of the incoming beam to match that of the outgoing beam. Hence the lens system can be uniquely determined given the two input requirements, the working distance 16 and the depth of field 22.

Forming microlenses out of graded index materials ('GRIN') is the preferred embodiment for the probes described herein, although lenses created from curved surfaces can be effectively used as well. The essential ingredient of a GRIN lens is the radial variation in the material index of refraction which causes the phase front to be bent in a way analogous to the phase bending in a conventional curved-surface lens. A simple instructive relationship between GRIN lenses and standard curved lenses can be formed by treating both as 'thin' lenses; essentially considering the length within the lenses as negligible. This relationship is:

$$\frac{n_1 - n_0}{R_l} = n_c \frac{A}{a^2} l_{grin}, \quad (3)$$

where $n_c$ is the center index of the GRIN material, A is the index gradient such that $$n_r = n_c \left(1 - \frac{A}{2}\right)\left(\frac{r}{a}\right)^2 \quad (4)$$

where $n_r$ is the index at radius r from the center, $I_g$ is the length of the GRIN material (Here the length is needed only to determine the focusing power of the 'thin' GRIN lens.), and a is the radius of the GRIN lens. Such materials are commercially available as mentioned earlier. However, generally commercially available GRIN lenses do not exist to meet the present imaging requirements because the gradient profile A and the size of the GRIN material (a) are such that the simultaneous achievement of the working distance 16 and depth of field 22 which are required here cannot be met.

Thus in one embodiment, customized GRIN materials are grown for the requirements described herein. In order to do this successfully, a more rigorous calculation is required, taking into account the length of the GRIN material for beam propagation as well as focusing strength. That is, as the Gaussian beam propagates through the GRIN material it is continuously modified by the gradient profile. Because the lenses here have requirements for relatively both large apertures and low focusing powers they cannot be considered 'thin' lenses as above.

Thus to calculate the required GRIN gradient profile, the well-known ABCD matrix formalism for treating Gaussian beam propagation in the paraxial approximation may be used. The ABCD matrix describing the propagation from the single mode fiber, through the GRIN material, and into the medium interface is given by:

$$\begin{bmatrix} A & B \\ C & D \end{bmatrix} = \begin{bmatrix} \cos(l_{grin}A') & \frac{n_{smf}}{n_c A'}\sin(l_{grin}A') \\ -\frac{n_c A}{n_0}\sin(l_{grin}A') & \frac{n_{smf}}{n_0}\cos(l_{grin}A') \end{bmatrix} \quad (5)$$

Where A' is $(\sqrt{A})/a$, and $n_{smf}$ is the index of the single-mode fiber. As is known in the art, the ABCD law for the transformation of Gaussian beams can be used here to solve for the A' parameter, given the other material parameters and, as before, the desired depth of field 22 and working distance 26. With some algebraic manipulation, two equations can be derived:

$$\frac{1}{\omega_f^2} = \frac{1}{\omega_i^2}\left(\cos^2(l_{grin}A') + \left(\frac{n_c A' \pi \omega_i^2}{\lambda}\right)^2 \sin^2(l_{grin}A')\right) \quad (6)$$

$$\frac{1}{W_D} = \left(\frac{n_{smf}}{n_0}\right)^2 \frac{1}{\sin(l_{grin}A')\cos(l_{grin}A')\left(\left(\frac{\pi\omega_i^2}{\lambda_{smf}}\right)^2 \frac{n_c A'}{n_0} - \frac{n_{smf}^2}{n_c n_0 A'}\right)} + \frac{n_c A'\sin(l_{grin}A')}{n_0\cos(l_{grin}A')} \quad (7)$$

where $w_f$ is the final (imaged) beam waist radius, $w_i$ is the initial beam waist radius at the exit of the single mode fiber, $\lambda$ is the free-space wavelength, $\lambda_{smf}$ is the wavelength inside the single mode fiber, and $W_D$ is the working distance (e.g. location of the imaged waist). For example, given a desired depth of field of 4 mm and a working distance of 3 mm, with $\lambda$ equal to 1.32 μm, Equations (7) and (8) can be iteratively solved to yield A'=1.2074 mm$^{-1}$ and $l_{grin}$=1.41 mm, starting with standard Corning SMF-28 fiber and imaging in air.

If the exact GRIN parameters cannot be achieved, especially the gradient coefficient A which in these designs is significantly lower than commercially available GRIN fibers, it is possible, as is known in the art, to affix an intermediate piece of fiber between the single mode fiber and the GRIN material. The purpose of this intermediate piece of fiber is to allow the beam to expand as it exits the single mode fiber and before it enters the GRIN fiber. This intermediate piece is preferably pure silica so it will have no beam shaping or guiding effects other than simple expansion. The combination of the expander and GRIN material allow a wider choice of gradient coefficients to be used and still achieve the desired working distance and depth of field.

Adding the expander in the ABCD formalism is particularly easy because the matrix for the expander, $$\begin{bmatrix} A & B \\ C & D \end{bmatrix} = \begin{bmatrix} 1 & L \\ 0 & 1 \end{bmatrix} \quad (8)$$

need only multiply the matrix for the GRIN lens. If there are index differences between the expander and the GRIN lens, additional matrices accounting for the index difference can be inserted into the equation.

Figure 3:
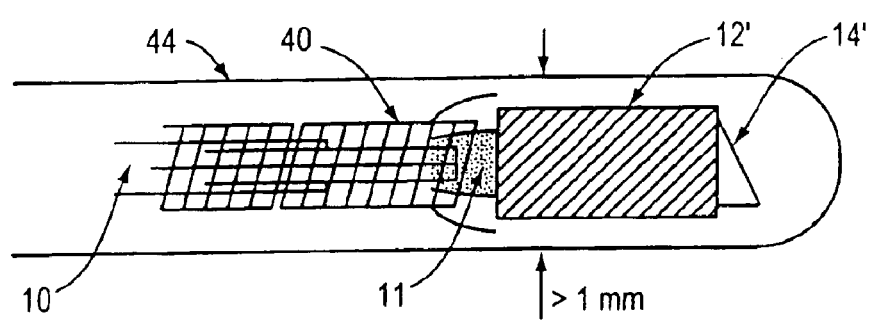
FIG. 3 illustrates an embodiment of a device known to the prior art.

FIG. 3 depicts an embodiment of a miniature imaging probes known to the art. In this embodiment, a single-mode fiber 10 (in one embodiment 125 μm in diameter) is glued using ultraviolet-cured optical adhesive 11 ('UV glue') to a commercially available 700 μm GRIN lens 12', which is, in turn, UV glued to a 700 μm beam director prism 14'. This optical transmission system is contained inside a rotatable torque cable 40 that is affixed near the proximal end of the GRIN lens 12'. The entire assembly is contained within a sheath 44 that is transparent to the wavelength of light emitted by the single-mode fiber 10 or has a transparent window near the prism 14'. This imaging probe can achieve the resolution, depth-of-field, and spot sizes illustrated in FIG. 2.

However, even though the fiber is only 125 μm in diameter and the largest beam size required is less than 100 μm as seen in FIG. 2, the entire assembly is approximately 1 mm in diameter. This large diameter limits the use of this device to openings significantly greater than 1 mm. For example, in imaging within small blood vessels the outside diameter (OD) of the probe must be less than 350 μm for insertion in the guidewire lumens of existing catheters. Further, the design shown also suffers from large back reflections because it is difficult to match the indicies of refraction of the various elements. These back reflections can signifi-
cantly impact the imaging quality of the lens particularly in OCT applications. In OCT applications large back reflections lead to an effect known blindness, whereby a large reflection tends to saturate the front-end electronics, rendering small reflections undetectable.

Figure 4:
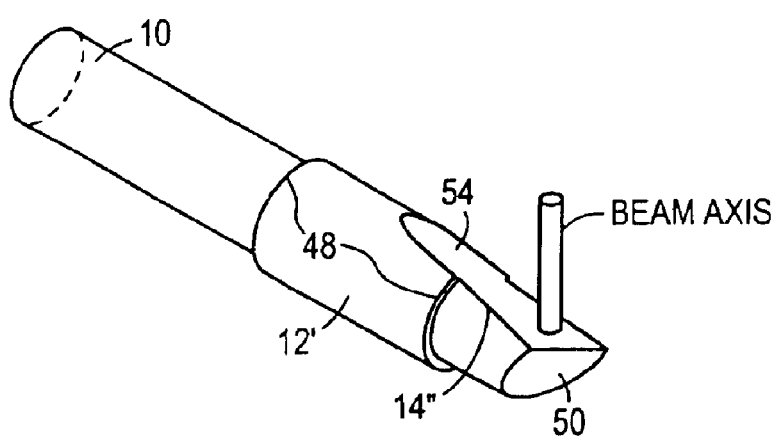
FIG. 4 illustrates an embodiment of the device constructed in accordance with the invention.

FIG. 4 depicts an embodiment of the optical assembly in which a single-mode transmission fiber 10 is attached to the GRIN lens 12', which in turn is attached a faceted beam director 14''. The attachments are done via fiber fusion splices 48, which eliminate the need for optical epoxy, although epoxy can be used if required. The beam director 14'' shown in this embodiment has two facets; the first facet 50 acts to reflect the light while the second facet 54 transmits the light and avoids beam distortions that would occur by passing light through the cylindrical fiber. In one embodiment the first facet 50 makes a 50 degree angle with the longitudinal axis of the fiber 10. Also in the embodiment, the second facet 54 makes a 5 degree angle with the longitudinal axis of the fiber 10.

The first facet 50 can then be either metal or dielectric coated or can be coated with a dichroic beam splitter to allow simultaneous forward and side viewing via different wavelengths. Alternatively, if the angle is greater than the angle for total internal reflection given by Snell's law (~43 degrees for a silica/air interface) then it is not necessary to coat the fiber. This results in a significant reduction in cost and complexity because coating the tip of the fiber for internal reflection (as opposed to much easier external reflection) is a significant technical challenge.

The total diameter of the optical lens 12'/beam director 14" in FIG. 4 can easily be made less than 300 μm while meeting the desired beam parameters, such as those shown in FIG. 2. Furthermore, the lens 12' can be made using standard fusion, splicing and polishing techniques and thus can be inexpensive, exhibit minimal back reflections and also focus precisely. It is preferred to make the attached beam director 14" of FIG. 4 by first fusion splicing a short section of coreless fiber to the GRIN lens 12', then polishing the fold mirror facet 50, and then polishing the exit facet 54 at the required angles.

Special attention must be given to the relationships between the angles of the facets 50, 54 when imaging using optical coherence tomography. Since the sensitivity of OCT systems routinely exceeds 100 dB, it is important to prevent back reflections from the second facet 54 from coupling back into the transmission fiber 10. Even a 4% reflection (silica to air interface) is strong enough to saturate and effectively 'blind' a sensitive OCT system. Thus, the angles must be chosen such that the back reflection angle is greater than the acceptance angle of the single-mode transmission fiber 10. For example, a reflection facet 50 polished with an angle of incidence of 50 degrees, and a transmissive facet 54 polished at 5 degrees to the axis of the lens, will return a beam exceeding the acceptance angle of standard SMF-28 single mode fiber 10. These particular angles offer another advantage; the 50 degree angle exceeds the angle for total internal reflection for a glass-air interface (nominally 43 degrees). Furthermore, this design allows the fiber 10 lens 12'/beam director 14" assembly to be tested in air prior to any coating process.

Figure 5:
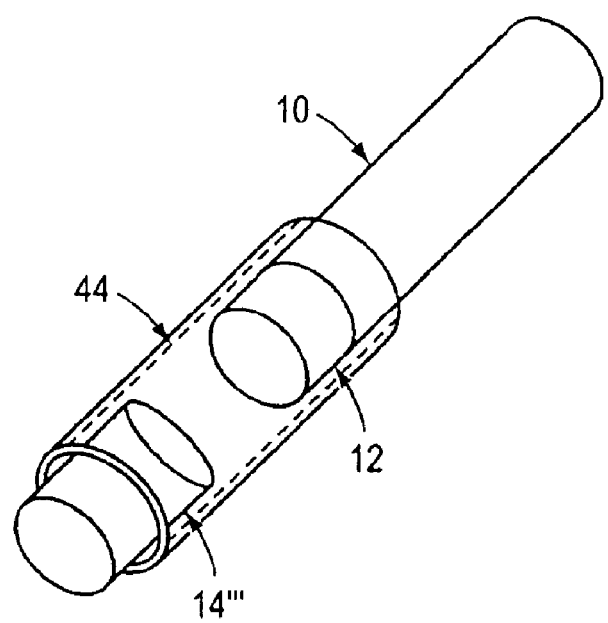
FIG. 5 illustrates an embodiment of a device with a detached fold mirror constructed in accordance with the invention.

FIG. 5 depicts another embodiment in which the beam director 14''' (fold mirror) is detached from the lens 12. This approach has the advantage of allowing the beam director 14''' mirror to be coated for external reflection, a substantially easier process. However, this approach offers the disadvantage that the length of the device increases and the focal length of the lens 12 must be increased to compensate. Due to the limited aperture of 125 μm diameter fibers 10, it is difficult to achieve both a long focal length and a small spot size, so compact beam director designs are generally preferred.

Figure 6A:
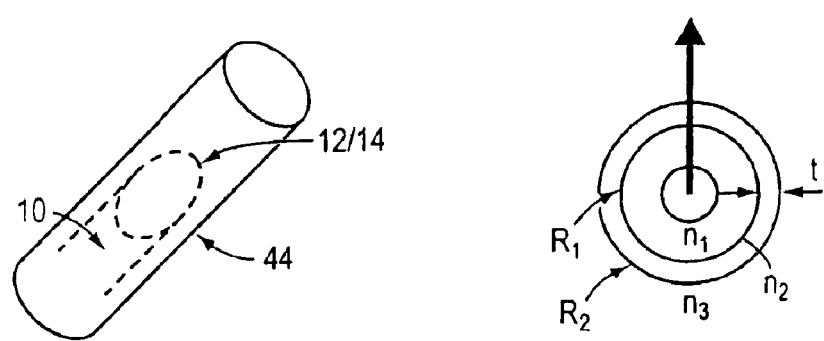
FIG. 6A illustrates an embodiment of an imaging wire inside a protective housing.

As shown in FIG. 6A, in each embodiment, the fiber 10 and lens 12 assembly are encased inside a protective sheath 44 or tube. The sheath 44 is required for several reasons. First and foremost is protection of the fiber 10. Second a sheath 44 improves the handling of long fiber catheters. Third the sheath 44 permits mechanical damping of the spinning fiber 10 to achieve uniform rotational speed, as detailed below.

However, the sheath 44 must allow the OCT light to exit with minimal loss and distortion to the outgoing beam in order to achieve the most optically efficient system possible. Without minimizing absorption, scattering, and distortion losses through the sheath 44, it is possible to lose more than 30 dB of system sensitivity. Of these losses, optical distortion is the more difficult to control (in a cylindrical sheath) and can account for 15–20 dB of loss. The distortion occurs as the beam passes through the curved surface of the sheath 44 which acts as lens. The power of lens is governed by the radius of the sheath 44 and the index differences between the sheath 44 and surrounding medium(s).

The sheath 44 may itself be transparent, or it may incorporate a suitable transparent material in the region of the beam director 14. A transparent sheath 44 is preferred since there are many materials that minimize absorption and scattering losses for OCT while still exhibiting good mechanical properties. Materials with these properties include Teflon, acrylic, polycarbonate, and several thermoplastics, such as Hytrel® from E.I. du Pont de Nemours Company. Hytrel is a thermoplastic polyester elastomer. Note that several of these materials can be opaque at visible wavelengths while still transmitting OCT wavelengths. A transparent sheath is also preferred since it allows the rotating fiber to be translated longitudinally within the sheath to perform three dimensional imagining without moving the sheath and fiber back and forth as a unit.

Flat window materials, or flats formed on the sheath 44 can of course be used to minimize the optical distortion effects, which makes the optical image properties easier to deal with, but greatly increases the fabrication complexity and costs. Also flat windows cannot be made to accommodate 360-degree scanning as required in a circumferential scanning device. If cylindrical sheaths 44 or windows are chosen, consideration must be given to the effects on the image quality that the window material and shape will impart.

Standard equations from classical (circular) optics give a good insight into the nature of the problems encountered:

$$\frac{n_1}{f_1} = \frac{n_2}{f_2} = \frac{n_2 - n_1}{R_1} - \frac{n_2 - n_3}{R_2} + \frac{(n_2 - n_3)(n_2 - n_1)t}{n_2 R_1 R_2} \quad (9)$$

where $n_1$ is the optical index in the medium to the left of the sheath, $n_2$ is the index of the sheath material itself, $n_3$ is the index in the medium to the right of the sheath, $R_1$ is the inner radius of curvature, $R_2$ is the outer radius, $f_{1,2}$ are the focal lengths to the left and right of the sheath, and t is the sheath thickness. In the case of the cylindrical sheath, the focal lengths in equation (9) apply only to the circumferential direction.

The optical effect of the sheath 44 on the transmitted beam is twofold. First, referring again to FIG. 1, the beam waist size 24 changes and second the location of the waist 20 changes. The coupling loss compared to the ideal case is best calculated by overlap integrals, but a good approximation for the one-dimensional additional loss in the circumferential direction is:

$$\eta = \frac{1}{1 + \frac{L}{z_0}} \quad (10)$$

where is the efficiency L is the distance from the circumferential beam waist to the ideal beam waist, and $z_0$ is the Rayleigh range, defined earlier.

It is apparent from examining the above equations that to minimize the optical effects of the sheath 44 (i.e., drive the focal lengths $f_1$ and $f_2$ towards ∞ which is the equivalent of a flat surface), the most important issue is matching (equalizing) the three indices, followed by decreasing the thickness, followed by increasing the radius of curvatures. It is understood that the above equation is for a spherical surface, whereas here the effect is only in the direction perpendicular to the sheath axis. However, this serves to illustrate the effect. Generally, it is very difficult to match all three material indices; minimizing the thickness introduces mechanical integrity concerns; and increasing the radius leads to unacceptably large probe diameters.

Another possibility is effectively 'neutralizing' the effect of the curved surface by choosing a medium inside the sheath such that the two refractive effects (inside and outside diameter of the sheath/window) cancel each other to first order. Choosing the proper index 'neutralizing' fluid can be accomplished using the following relationship:

$$\frac{n_2 - n_1}{R_1} = \frac{n_2 - n_3}{R_2} \tag{11}$$

Here $n_1$ is the optical index of the neutralizing fluid or gel, $n_2$ is the index of the window material, and $n_3$ is the index of the surrounding medium. This approach gives one new degree of freedom, making it possible to balance the sheath size, thickness and available fluid indices to neutralize the optical effects to first order (e.g. reduce the effects to less than 10% of their original levels).

Figure 6B:
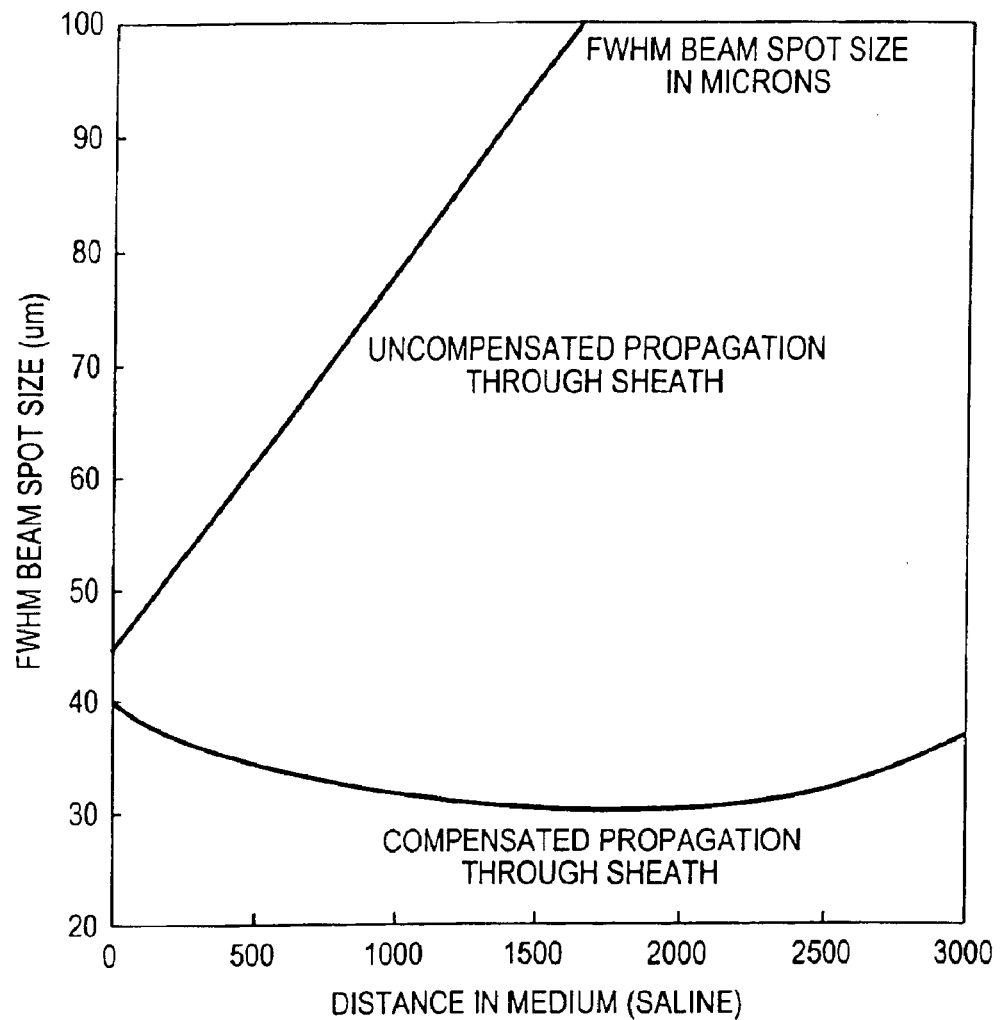
FIG. 6B illustrates an embodiment of optically compensated and uncompensated propagation through a sheath.

The effect of the neutralizing fluid is shown in FIG. 6B. The uncompensated curve 60 is for an air-filled acrylic sheath, 355 um in diameter and 50 microns thick, using a fiber lens 12 designed to produce a 30 $\mu$m waist at a depth of 2 mm into saline. The uncompensated case has a rapidly diverging beam, giving an extrapolated waist of 6 um located approximately 400 $\mu$m to the left of the interface. The compensated curve 64 is also shown, using a commercially available fluorosilicone fluid, which gives a circumferential waist near 1800 $\mu$m—very close to the ideal. The overall coupling losses are over 12 dB in the uncompensated case and less than 1 dB in the compensated case representing a 90% reduction in unwanted losses.

To avoid the complication of coating the internally reflective facet 50, total internal reflection is preferred. As noted, for a glass/air interface this occurs for any angle of incidence greater the 43 degrees. However, once the fiber is immersed in an environment such as water or saline in which the refractive index is much larger than unity (air), total internal reflection becomes impractical. Thus it is desirable to maintain the glass/air interface.

Figure 7:
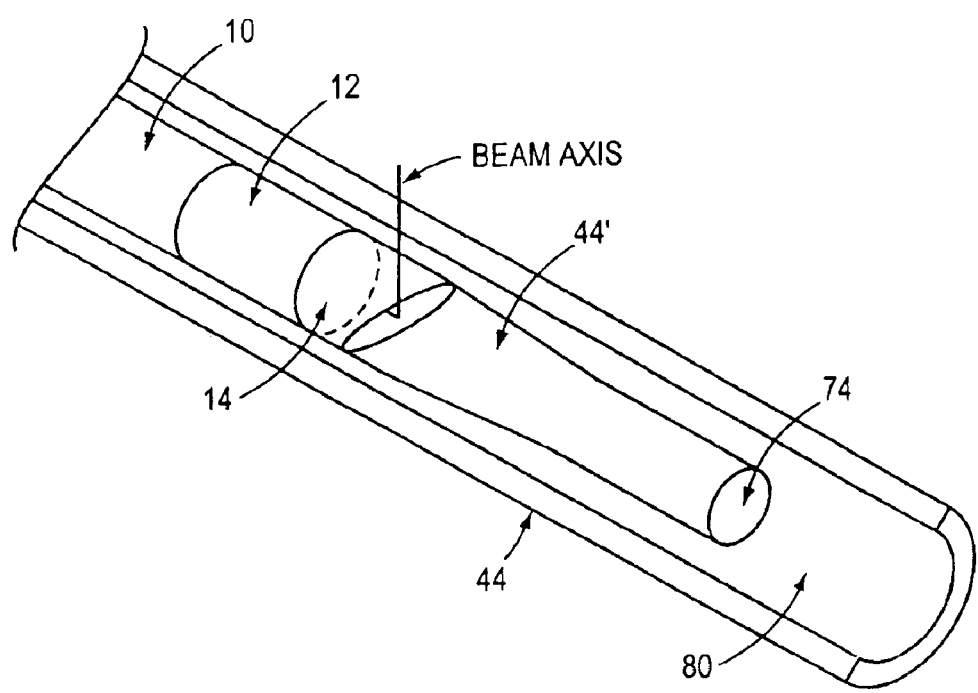
FIG. 7 illustrates an embodiment of the invention with an optically transparent viscous damping fluid.

FIG. 7 depicts a preferred method for achieving an air-backed beam director 14 such that total internal reflection can be used at practical angles within a fluid environment. A thin transparent inner sheath 44' is attached over the lens 12/beam director 14 and sealed 74 at the distal end. The inner sheath 44' may be attached by optical epoxy or by heat-induced shrinkage. The outer sheath 44 of FIG. 6A is also shown in FIG. 7.

Once the optical effects have been addressed, it is crucial to perform uniform rotational scanning so that high quality, understandable, and reproducible images may be obtained. In the endoscopic imaging industry, much effort has been devoted to this problem. Essentially three viable techniques have evolved in the prior art. The first is the development of torque wires 40, already discussed. The second is the development of phased array systems (in ultrasound imaging), which can effectively steer the beam via electronic control of the distal transducers. Lastly, software image correction can try to compensate for NURD by post-processing the image.

As mentioned, torque wires 40 are generally not scalable to the sizes considered here and add significant cost. Phased array systems are highly complex since they involve many transducers and additional control electronics. Multiple fiber solutions are possible, but add significant costs. Lastly the software-based correction is quite complex and fallible and the resultant image is generally of much poorer quality than if the NURD had been prevented a priori.

A new method for controlling rotational speed variances for fiber optic probes is disclosed and described herein. Given the very low torsional stiffness of the glass fibers (as detailed earlier), significant winding of the fiber can be expected over a length and rotational speed practical for many applications, especially medical applications. For example, a 2 meter length of 125 um diameter fiber coated with 7.5 m of a polyimide coating, spinning at 10 Hz inside a water-filled catheter housing experiences over 10 complete turns of winding. Although the distal tip must spin on average at 10 Hz it will experience speed variations, (NURD) during fractions of a rotation due to winding and unwinding caused by frictional variations, slight eccentricities in the glass fiber itself, catheter movements, temperature variations, and so forth.

Figure 8:
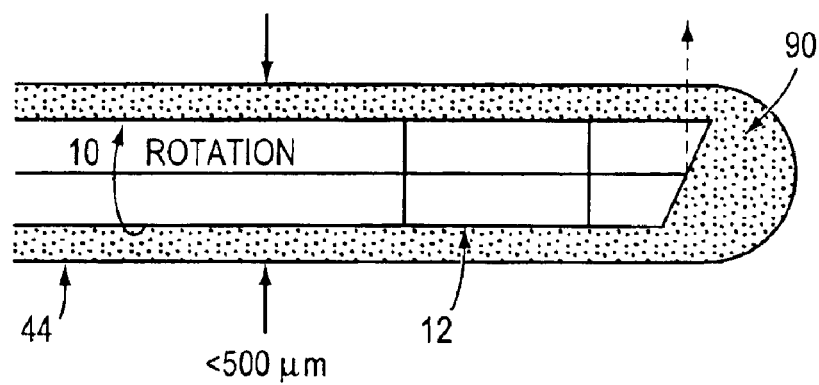
FIG. 8 illustrates an embodiment of the invention utilizing total internal reflection inside a optical viscous fluid.

As conceptually depicted in FIG. 8 (as well as FIG. 7), it is possible to control these speed variations by using negative feedback control of the speed at the distal tip of the optical transmission system. Viscous damping localized at the tip can provide this feedback control. Introducing a viscous damping fluid 90 between the optical transmission system and the sheath 44 creates, in essence, an optically transparent journal bearing. An optical path is shown by the dotted arrow. The mechanical properties of journal bearings are well understood and documented thoroughly. Several relationships are:

$$ShearStress(\tau) = \mu \times \frac{V}{a} = \mu \times RPS \times \frac{2\pi r}{a} \tag{12}$$

$$\text{Torque} = \mu \times RPS \times \frac{2\pi r}{a} \times 2\pi r \times l \times r \tag{13}$$

$$\frac{\text{Windup}}{\text{length}} = \frac{\text{Torque}}{G \cdot I_z} \tag{14}$$

where is the viscosity, a is the clearance between the fiber and the sheath, V is the velocity, RPS is revolutions per second, l is the length over which the viscous fluid is applied within the sheath, G is the shear modulus (modulus of rigidity of the fiber), and $I_z$ is the moment of inertia about the axis of the fiber.

Since the viscosity-induced torque loading increases with speed and will act to slow down an unwinding fiber, the negative feedback is established. By controlling the variables a, l, and it is possible to precisely control the rotational characteristics of the distal end of the optical transmission system. This technique offers the advantage of controllability, low cost, low complexity, and negligible increase in probe size while permitting NURD-free operation of endoscopic imaging systems. Even more control of NURD can be had, for instance, by placing different viscosity fluids at different locations where the inherent high viscosities help prevent mixing except near the fluid boundaries. This facilitates the isolation of the various fluids while still allowing free rotation. Distributing a viscous fluid over the entire length of the catheter is also possible, but distally located viscous damping is usually more effective for NURD control.

Finally, the fluid used for viscous control must also possess the required transmissive and preferably neutralizing optical characteristics as detailed earlier. There are a number of fluids and gels, for example fluorosilicone compounds, that are suitable both optically and mechanically for the purposes described herein. In addition, suitable viscous damping fluids typically have a kinematic viscosity index of between 500 and 20,000 centistokes and an optical index of refraction between 1.32 and 1.65 in some embodiments.

Several classes of compounds meet these requirements, fluorosilicones, syrups, synthetic and natural oils, even radiographic contrast agent used in many interventional cardiology procedures (such as RenoCal-76 ™, a solution of Diatrizoate Meglumine and Diatrizoate Sodium, manufactured by Bracco Diagnostics of Princeton N.J.).

Many viscous fluids exhibit a strong interdependency between viscosity and temperature. This can be used advantageously in various embodiments. Temperature effects can detrimentally impact the use of viscous fluids in some embodiments. One aspect of the invention relates to regulating viscous fluid temperatures in order to achieve a reduction in NURD. For example, an advantageous use of the temperature dependence is heating the viscous damping fluid to facilitate easy injection into a tight orifice, such as a long catheter sheath. A potentially detrimental effect is seen in intravascular imaging applications, where saline flushes are often used. If the saline is not at body temperature, the viscosity of the viscous damping fluid will change and the delivery fiber will wind or unwind (depending on whether the viscosity increases or decreases), causing the observed OCT image to spin. A simple solution is to ensure that any injected saline, or other suitable catheter flush, is maintained at or near body temperature. An example of this temperature sensitivity is given by MED-360, a silicone fluid manufactured by NuSil of Carpinteria, Calif. For Med-360, the viscosity at room temperature (25 C.) is 1010 centistoke and drops to 750 centistoke at body temperature (38 C.).

Figure 9:
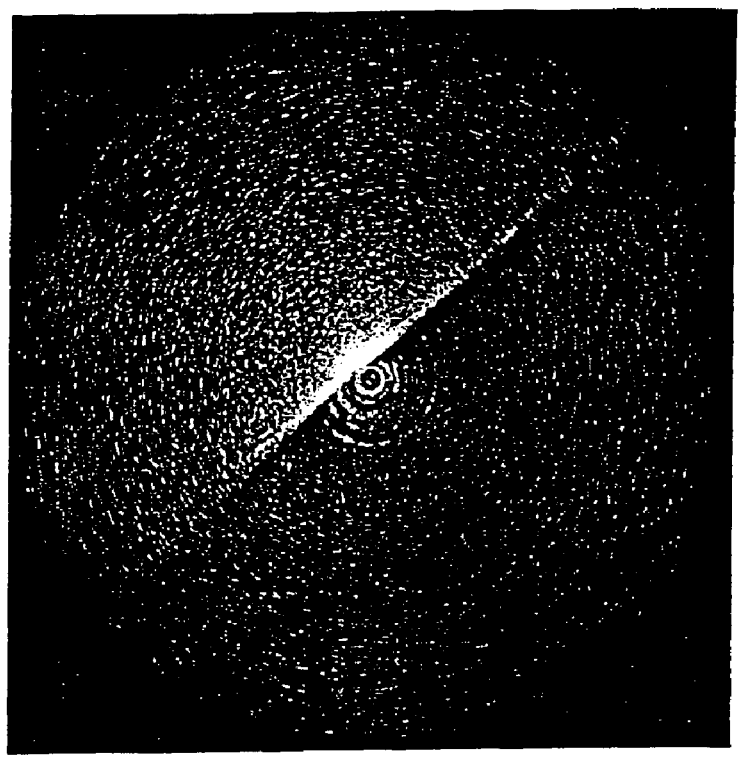
FIG. 9 illustrates the use of the invention for imaging of a flat surface using NURD compensation.
Figure 10:
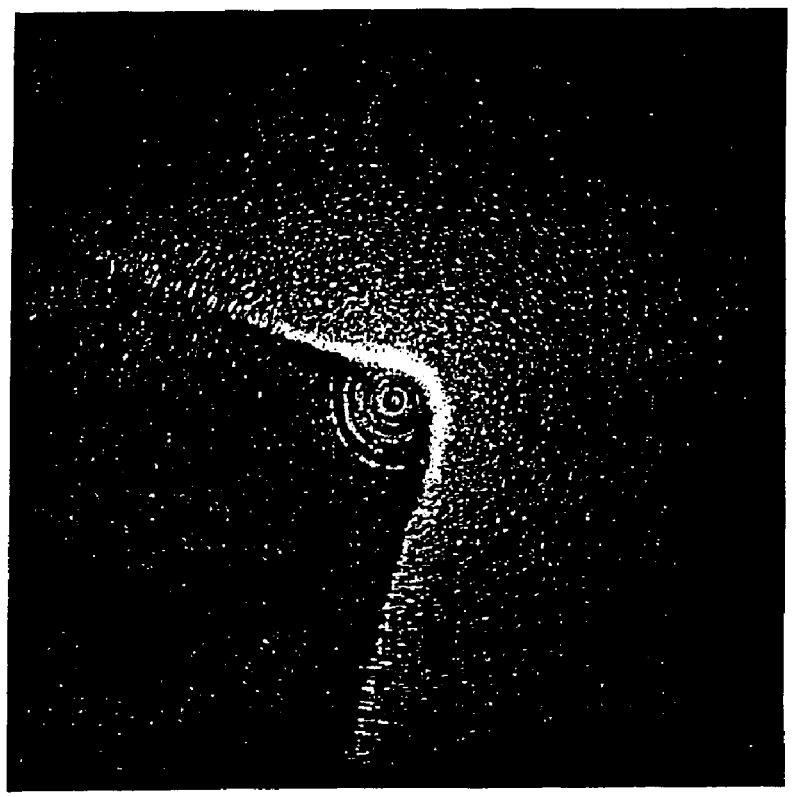
FIG. 10 illustrates the imaging of a flat surface without NURD compensation.
Figure 11:
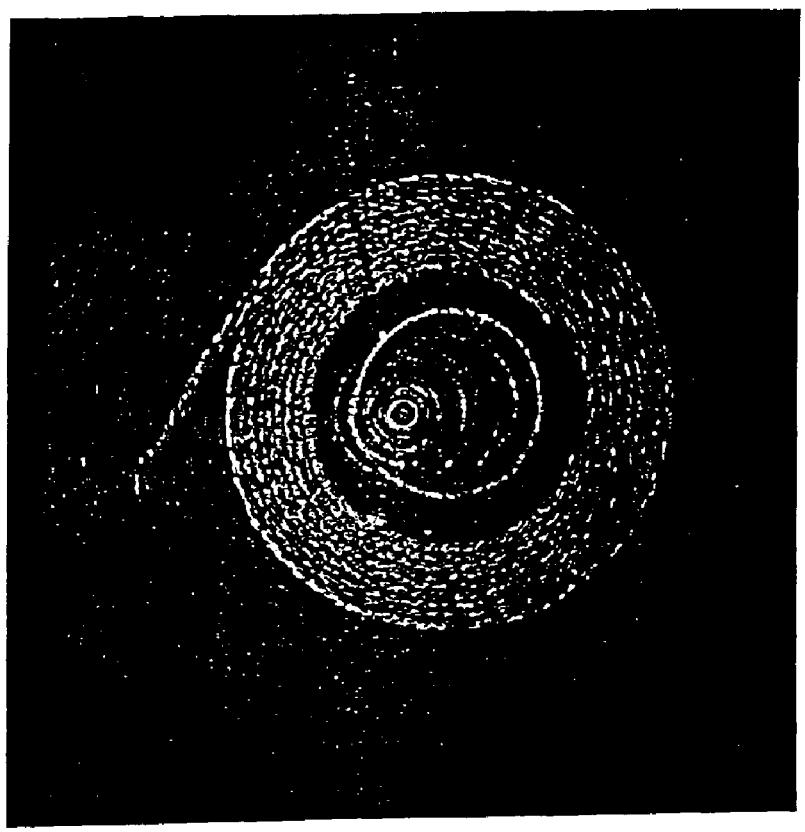
FIG. 11 illustrates the use of the invention for imaging the inside of cylindrical tissue phantom using NURD compensation.
Figure 12:
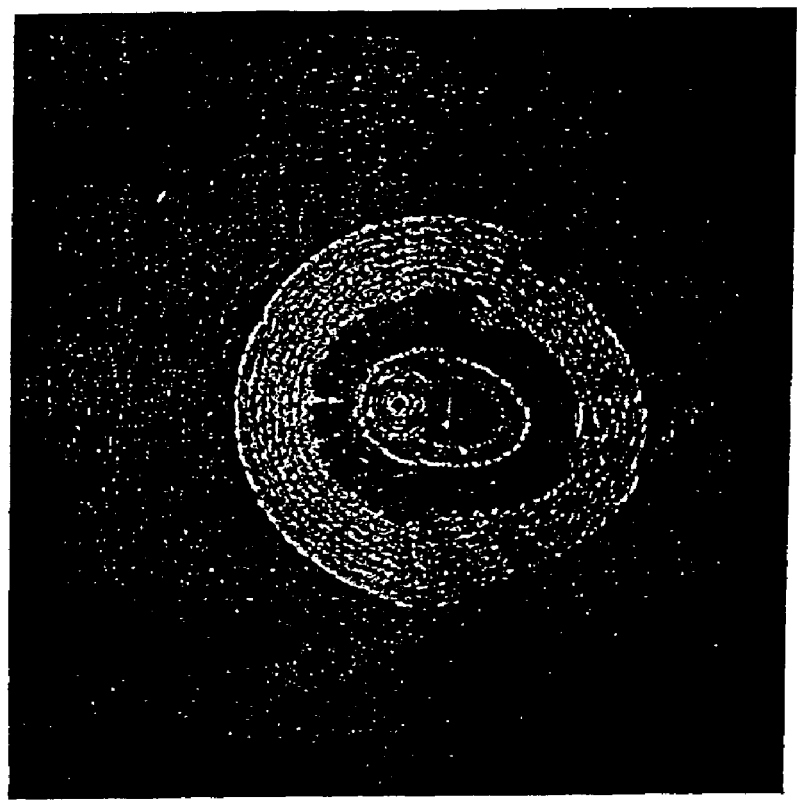
FIG. 12 illustrates the imaging of the inside of cylindrical tissue phantom without NURD compensation.

FIG. 9 depicts a NURD-free optical coherence tomographic image of a flat surface obtained using the catheter shown in FIG. 7. FIG. 10 is an image of the same surface obtained without the viscous fluid damping used to obtain the NURD free image of FIG. 9. Similarly, FIG. 11 is a NURD-free optical coherence tomographic image of the inside of a cylindrical tissue phantom obtained using the catheter shown in FIG. 7. FIG. 12 is the image of the same cylindrical tissue phantom obtained without viscous fluid damping. In both FIGS. 10 and 12 the distortion of the image is apparent due to the irregular rotational speed of the optical probe tip.

It is worth noting, that the concept of a distally located viscous fluid for NURD reduction can be applied to situations other than fiber optic imaging. For example an ultrasound catheter can use this technique in place of the standard and expensive torquewires.

Although this discussion has focused on medical applications it is clear that there are a large number of non-medical applications in industrial inspection and materials analysis that are possible. Furthermore, while single-mode fibers are preferred for OCT imaging, multimode fibers may be used as well in the embodiments described herein.

Figure 13:
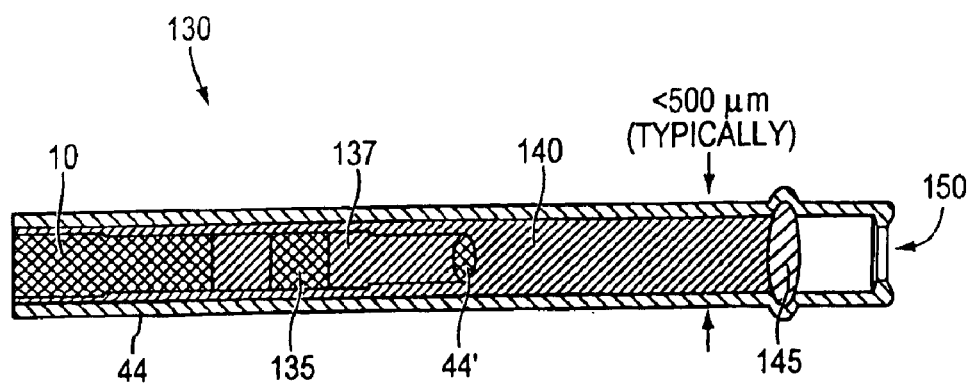
FIG. 13 illustrates a miniature optical probe in accordance with an illustrative embodiment of the invention.

The interrelation of some of the various elements of the invention are shown in the illustrative embodiment of the probe 130 shown in FIG. 13. A single mode fiber 10 is shown disposed within an inner sheath 44' of the probe 130. The inner sheath 44' typically has a sealed air gap. A focusing element 135 is shown in communication with a beam director 137. Both the focusing element 135 and the beam director 137 are disposed within the inner sheath 44'. The inner sheath is disposed within an outer sheath 44 as has been previously described in various embodiments. A viscous damping fluid 140 is disposed within the outer sheath 44 and surrounds a portion of the inner sheath 44'. In some embodiments, the entirety of the inner sheath 44' is surrounded by the viscous damping fluid 140. The diameter of the outer sheath 44 is under 500 micrometers in various embodiments as shown. A sealing ball 145 is typically disposed within the outer sheath to contain the viscous damping fluid 145 within a defined volume. A heat formed tip 150 is also present in various embodiments.

What is claimed is:

1. An optical probe comprising:
    a sheath;
    a flexible, bi-directionally rotatable, optical transmission system positioned within said sheath, the optical transmission system comprising a transmission fiber, the transmission fiber capable of winding in response to rotation of the transmission system, said optical transmission system capable of transmitting, focussing and collecting light of
    a predetermined range of wavelengths; and
    a viscous damping fluid located in said sheath,
    wherein both said sheath and said viscous damping fluid are transparent to at least some of said wavelengths of light,
    wherein the index of refraction of said viscous fluid is chosen to substantially remove cylindrical optical distortion induced by propagation through said sheath and to reduce rotational speed variations at least partially induced by winding the transmission fiber.

2. The optical probe of claim 1 wherein said optical transmission system is less than substantially 300 μm in diameter.

3. The optical probe of claim 2 wherein said optical transmission system comprises:
    a focusing element optically coupled to a beam director.

4. The optical probe of claim 1 wherein said transmission fiber is rotatably driven at a proximal end.

5. The optical probe of claim 3 wherein said focussing element and the beam director comprises the transmission fiber attached to a first segment of coreless silica fiber, attached to a graded index fiber, attached to a second segment of coreless fiber, wherein said second segment of coreless fiber has one or more angled facets to form the beam director.

6. The optical probe of claim 5 wherein said angled coreless fiber is reflectively coated on one angled facet.

7. The optical probe of claim 5 wherein said angled coreless fiber has a first facet angle such that the beam director directs the beam using total internal reflection.

8. The optical probe of claim 5 wherein said second segment of said angled coreless fiber is coated on one facet by a dichroic coating such that optical energy is reflected substantially at one wavelength region and optical energy is transmitted at a substantially separate second wavelength region.

9. The optical probe of claim 3 wherein said focussing element and beam director comprises:
    a transmission fiber attached to a piece of graded index fiber having an end face, the transmission fiber's working aperture and index profile are designed to produce a beam waist of less than 100 μm in radius at a working distance measured from the end face of up to ten millimeters in either air or fluid; and
    a faceted piece of coreless fiber attached to the graded index fiber.

10. The optical probe of claim 3 wherein said beam director comprises two facets, a first facet acting as a reflector and a second facet acting as a transmissive element, wherein an angle of residual back reflected light arising from the second facet and re-reflecting from the first facet through the focussing element exceeds an acceptance angle of the transmission fiber.

11. The optical probe of claim 1 wherein said optical transmission system creates:
an exit beam waist less than 100 μm in radius with a working distance ranging from 0 to ten millimeters, and a depth-of-field to 10 mm.

12. The optical probe of claim 11 wherein said working distance and depth of field are applicable to either air-based or fluid based imaging conditions.

13. The optical probe of claim 1 wherein said sheath is less than substantially 500 μm in diameter.

14. The optical probe of claim 1 wherein said viscous damping fluid is contained at least within a distal portion of the sheath.

15. The optical probe of claim 3 wherein the transmission fiber is slidably rotatable within said sheath.

16. The optical probe of claim 1 wherein said sheath comprises a plurality of regions, each region having a predetermined length and containing a fluid with a predetermined viscosity index.

17. The optical probe of claim 1 further comprising a lumen for providing catheter flushes.

18. The optical probe of claim 17 wherein catheter flushes are maintained at body temperature to minimize temperature-induced viscosity changes at a distal tip of the catheter.

19. An optical probe comprising:
an optical transmission system designed to operate at a predetermined wavelength range, said optical transmission system comprising:
a first sheath defining a bore, said first sheath sealed at a distal end;
a beam director located within said bore of said first sheath;
a focusing element located within said bore of said first sheath and optically coupled to said beam director located within said bore of said first sheath;
a second sheath defining a bore, said first sheath located within said bore of said second sheath;
a viscous damping fluid located within said bore of said second sheath, wherein an index of refraction of said fluid is chosen to substantially remove optical cylindrical distortion of the beam propagation through said second sheath;
a rotatable optical fiber located within said bore of said second sheath such that winding and unwinding of the rotatable optical fiber is regulated by the viscous damping fluid; and
wherein said first sheath is closed at its distal end and said optical transmission system is enclosed within said first sheath.

20. The optical probe of claim 19 wherein said optical transmission system is less than substantially 300 μm in diameter.

21. The optical probe of claim 19 wherein said optical transmission system creates an exit beam waist less than 100 μm in radius with a working distance ranging from 0 to ten millimeters, and a depth-of-field up to ten millimeters.

22. The optical probe of claim 19 wherein said beam director utilizes total internal reflection by an angled facet.

23. The optical probe of claim 19 wherein said second sheath is less than substantially 500 μm in diameter.

24. The optical probe of claim 19 wherein said beam director has only a single internally reflecting facet.

25. The optical probe of claim 19 wherein said focusing element comprises a coreless fiber with a radiused tip.

26. The optical probe of claim 19 further comprising a lumen for providing catheter flushes.

27. The optical probe of claim 26 wherein catheter flushes are maintained at body temperature to minimize temperature-induced viscosity changes at the distal tip of the catheter.

* * * * *